(12) United States Patent
Jones (10) Patent No.: US 8,679,165 B1
(45) Date of Patent: Mar. 25, 2014

(54) CERVICAL PLATE HAVING GRADUATED THICKNESS

(71) Applicant: A. Alexander M. Jones, Savannah, GA (US)

(72) Inventor: A. Alexander M. Jones, Savannah, GA (US)

( * ) Notice: Subject to any disclaimer, the term of this patent is extended or adjusted under 35 U.S.C. 154(b) by 0 days.

(21) Appl. No.: 13/758,836

(22) Filed: Feb. 4, 2013

Related U.S. Application Data

(63) Continuation of application No. 12/313,919, filed on Nov. 25, 2008, now Pat. No. 8,366,752.

(60) Provisional application No. 61/004,501, filed on Nov. 27, 2007.

(51) Int. Cl.
*A61B 17/70* (2006.01)
*A61B 17/80* (2006.01)

(52) U.S. Cl.
USPC ............ 606/286; 606/246; 606/902; 606/903

(58) Field of Classification Search
USPC ...................... 606/70–71, 280–284, 902–906
See application file for complete search history.

(56) References Cited

U.S. PATENT DOCUMENTS 8,366,752 B1 * 2/2013 Jones ............................ 606/286

* cited by examiner

*Primary Examiner* — Sameh Boles
(74) *Attorney, Agent, or Firm* — Ramon L. Pizarro; Edwin H. Crabtree (57) ABSTRACT

A cervical plate is disclosed. The plate includes plate body with a first end adapted for attachment to a first vertebra in a cephalad relation to the plate body and a second end adapted for attachment to second vertebra in a caudad relation to the plate body. The plate body being of a first thickness at the first end and of a second thickness at the second end, the first thickness being smaller than the second thickness, and the plate body transitioning from the first thickness to the second thickness in a graduated manner.

4 Claims, 7 Drawing Sheets

CERVICAL PLATE HAVING GRADUATED THICKNESS

REFERENCE TO RELATED APPLICATIONS

This application is a continuation of my application having Ser. No. 12/313,919, filed on Nov. 25, 2008, titled "CERVICAL PLATE HAVING GRADUATED THICKNESS", now U.S. Pat. No. 8,366,752, issued Feb. 5, 2013, and is incorporated herein by reference in its entirety. My U.S. Pat. No. 8,366,752 claims the benefit of my provisional application having Ser. No. 61/004,501, filed Nov. 27, 2007.

BACKGROUND OF THE INVENTION (a) Field of the Invention

This invention generally relates to a device and method for fusing joining cervical vertebra. More particularly, but not by way of limitation, to a cervical plate having graduated thickness and a method for using the same.

(b) Background

The fusion of sections of the spine using plates that are mechanically fastened to the vertebra is a well-known method of treating problems associated with diseased or injured areas of the spine. The cervical region of the spine presents distinct anatomical limitations to the design and application of these plates. Cervical plate fusions are typically accomplished through the anterior of the cervix. Anterior cervical plates need to be thin (2-2.5 mm) to avoid esophageal injury, especially at mid to upper c-spine. Most degenerative disease occurs at C5-6, C6-7 Lower c-spine and C-thoracic anterior fixation is difficult because of anatomy (sternum). The ability to compress an inter-body graft at time of surgery is desirable, and believed to lead to increased fusion rate. Increased screw length leads to increased pullout strength with convergent (divergent) screws.

Vertebral body size increases from cephalad to caudad, while Sagittal roll increases from cephalad to caudad. Prevertebral space increases from cephalad to caudad.

SUMMARY

It has been discovered that the problems left unanswered by known art can be solved by providing a cervical plate that includes:

A plate body having:

A first end adapted for attachment to a first vertebra in a cephalad relation to the plate body;

A second end adapted for attachment to second vertebra a caudad relation to the plate body;

The plate body being of a first thickness at the first end and of a second thickness at the second end, the first thickness being smaller than the second thickness, and the plate body transitioning from the first thickness to the second thickness in a graduated manner.

It is preferred that the graduation between the first thickness and the second thickness be will be smooth, generally constant graduation in thickness. Stepped reductions in thickness will result in undesired stress concentrations.

A method of installing a plate such as the disclosed graduated thickness plate is also disclosed. The method includes the steps of locating the plate using guide wires at the extreme ends of the plate, drilling and inserting screws in plate holes between the guide wires, then removing the guide wires and drilling and inserting screws in the holes at the extreme ends of the plate.

It should also be understood that while the above and other advantages and results of the present invention will become apparent to those skilled in the art from the following detailed description and accompanying drawings, showing the contemplated novel construction, combinations and elements as herein described, and more particularly defined by the appended claims, it should be clearly understood that changes in the precise embodiments of the herein disclosed invention are meant to be included within the scope of the claims, except insofar as they may be precluded by the prior art.

DRAWINGS

The accompanying drawings illustrate preferred embodiments of the present invention according to the best mode presently devised for making and using the instant invention, and in which.

DETAILED DESCRIPTION OF PREFERRED EXEMPLAR EMBODIMENTS

While the invention will be described and disclosed here in connection with certain preferred embodiments, the description is not intended to limit the invention to the specific embodiments shown and described here, but rather the invention is intended to cover all alternative embodiments and modifications that fall within the spirit and scope of the invention as defined by the claims included herein as well as any equivalents of the disclosed and claimed invention.

Figure 1:
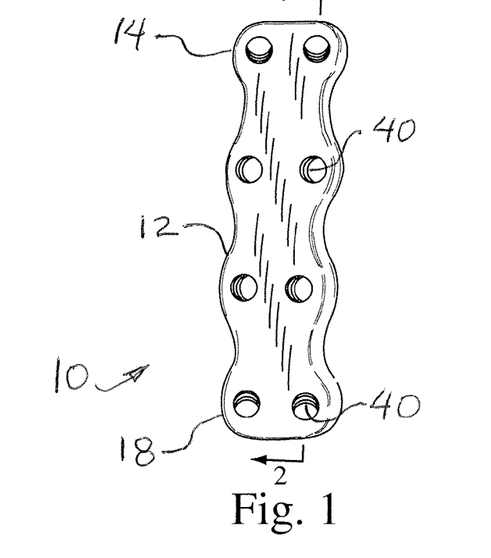
FIG. 1 is a perspective view of an example of the disclosed invention.
Figure 2:
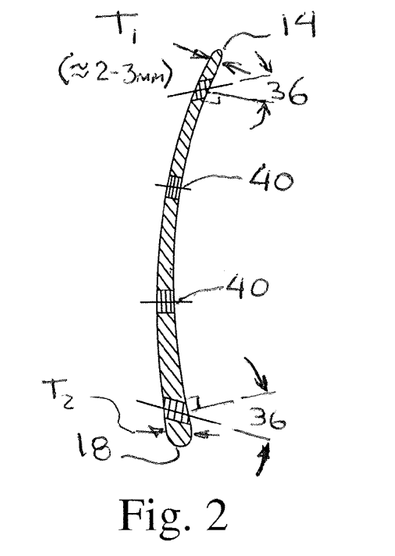
FIG. 2 is a section, taken along the line 2-2 of FIG. 1, and illustrates the graduated thickness, from the first thickness at the first, cephalad, end of the plate to the second, greater, thickness at the second, caudad, end of the plate.
Figure 3:
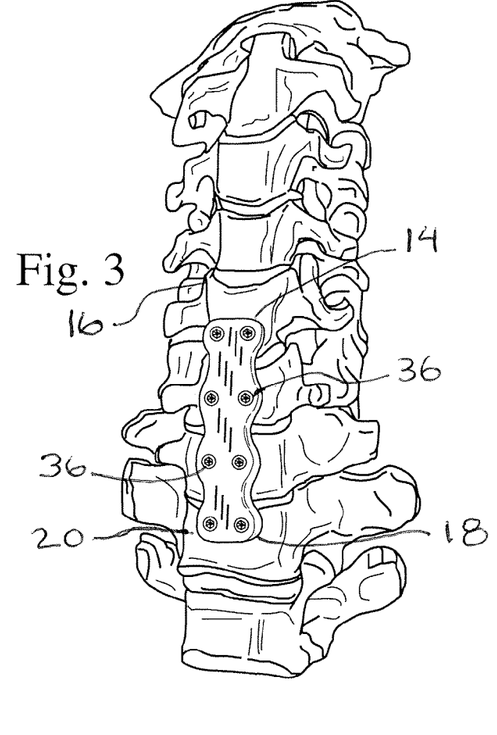
FIG. 3 illustrates the example from FIG. 1 installed.
Figure 4:
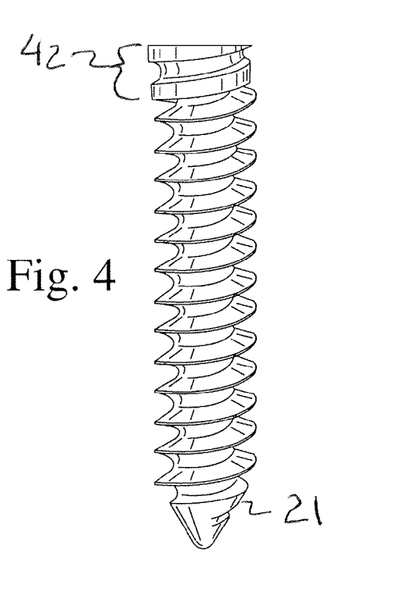
FIG. 4 illustrates an example of the preferred screws used with the disclosed invention. The figure showing the threads at the head of the screw, which are designed to cold weld though an interference with threads in the plate.
Figure 5:
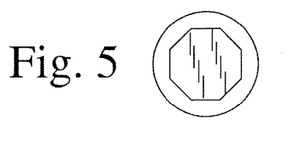
FIG. 5 is a top view of the head of the screw of FIG. 4, and shows a recess that mates with a tool (not shown) that is used to torque the screw until the weld is accomplished and the needed insertion is achieved.
Figure 6:
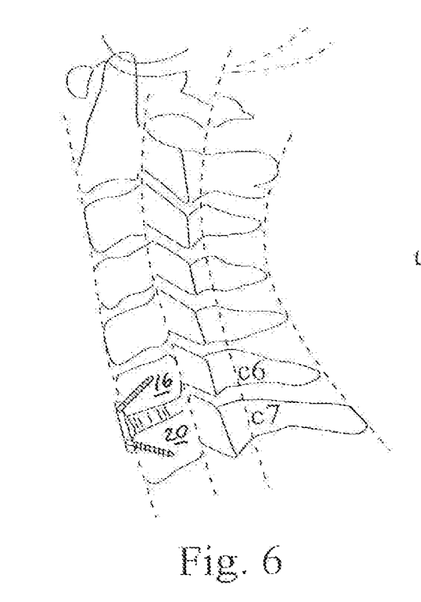
FIG. 6 illustrates an example of the disclosed invention as adapted for fusing C6 and C6 (a single level fusion).
Figure 7:
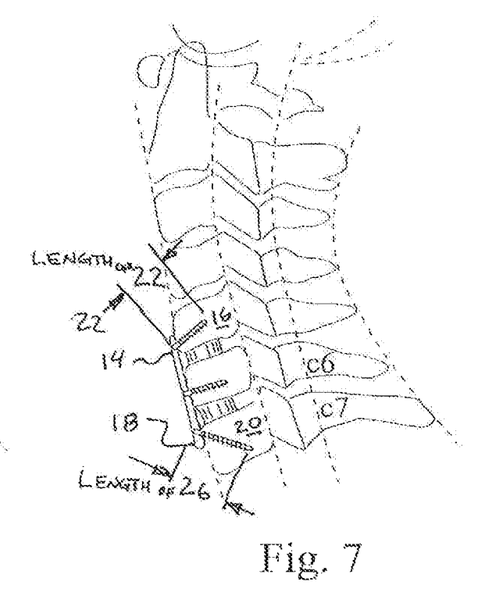
FIG. 7 illustrates the disclosed invention in a two-level fusion.
Figure 8:
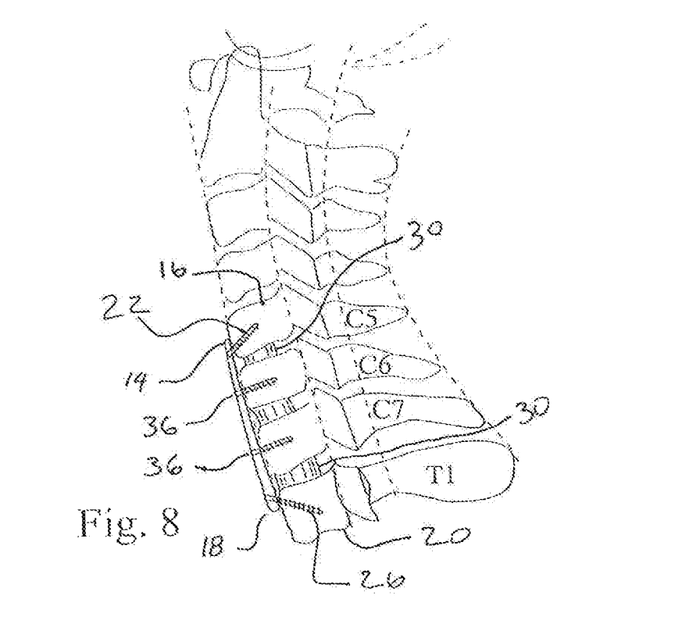
FIG. 8 illustrates the disclosed invention in a three-level fusion.

FIGS. 1 through 3 that it is contemplated that the disclosed graduated thickness cervical plate 10 will include a body 12 with a first end 14 that is adapted for attachment to a first vertebra 16 in a cephalad relation to the plate body 12. The plate 10 will also include second end 18 that is adapted for attachment to second vertebra 20 in a caudad relation to the plate body 12. The plate body 10 will be of a first thickness $T_1$ at the first end 14 and of a second thickness $T_1$ at the second end 18, the first thickness $T_1$ being smaller than the second thickness $T_2$, and the plate body transitioning from the first thickness to the second thickness in a graduated manner (gradually).

In a preferred example the first end 14 (cephalad) $T_1$ is about 2.3 mm. Graduated increases in plate thickness with increasing plate length. FIGS. 5-8 illustrate compression screws 21, at least one being a fixed angle compression screws of a first screw length 22 used in screw holes 24 located at the first end 14, and another being a fixed angle compression screws of a second screw length 26 are used in screw holes 24 at the second end 18. The compression screws of a second screw length 26 are longer than the fixed angle compression screws of a first screw length 22.

The disclosed invention provides biomechanical advantages through the use of thicker plate at the second end 18. The increased thickness provides increased resistance to plate and plate-screw bending with forward flexion. This in turn decreases graft 30 unloading at inter-space between the vertebra, and thus promoting fusion. Thus the disclosed plate is thicker where it is needed to resist bending. Longer screws are used at this more rigid screw-plate connection to provide firmer anchoring of the plate and thus provide more rigid retention of the vertebra, holding the vertebra firmly against the graft 30.

Anatomical Advantages

Increasing vertebral body size and increased sagittal roll caudally allows for longer larger screws at bottom of construct. This results in increased rigidity of the construct and provides increased pullout strength. The increased prevertebral space caudally (space between esophagus and vertebral column) allows for increased plate thickness.

Surgical Advantages

It will be understood that the disclosed plate system and method of implantation requires only simple, well-known, instrumentation and surgical techniques that are familiar to the surgeon. Angulation of screws (especially lower) allows for easier insertion, while creating the compression between the vertebra to enhance fusion.

Plate with Graduated Thickness Surgical Method

Figure 9:
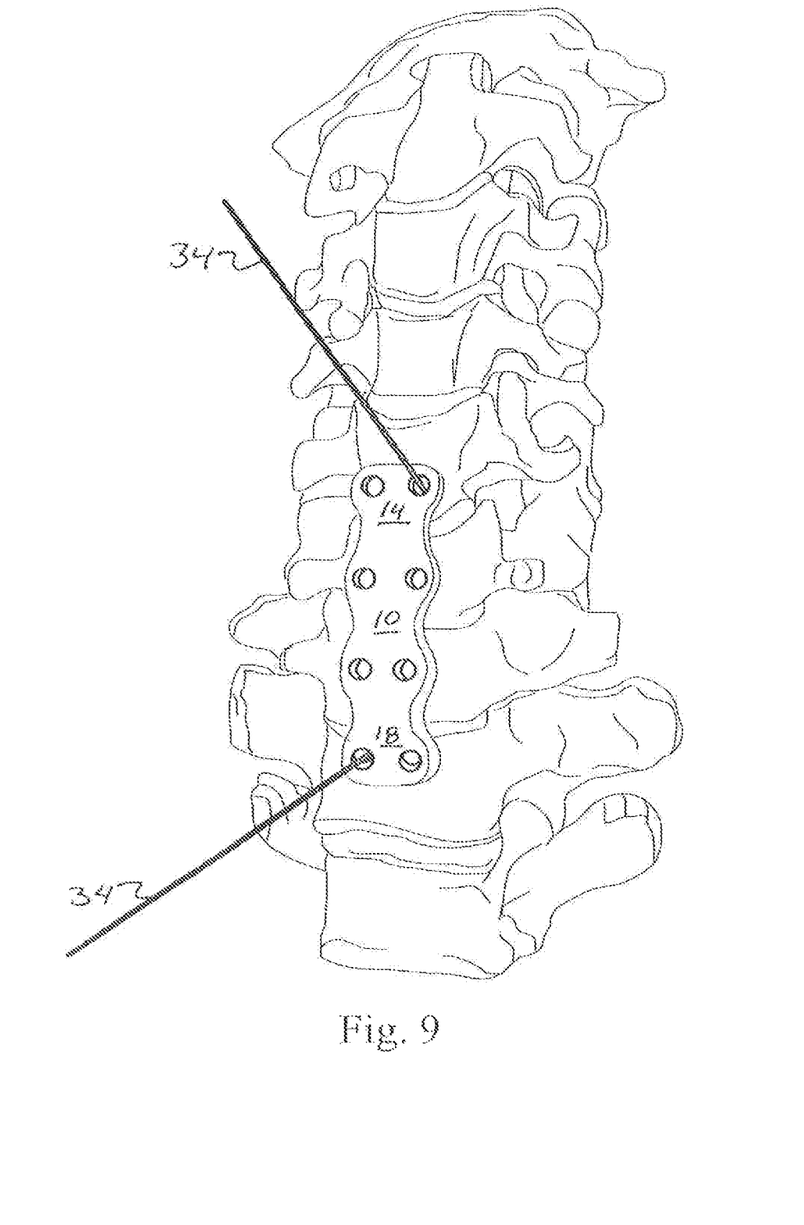
FIG. 9 illustrates the disclosed invention while using a pair of guide wires at the cephalad and caudad screw locations to position the disclosed plate in position prior to drilling screw holes.
Figure 10:
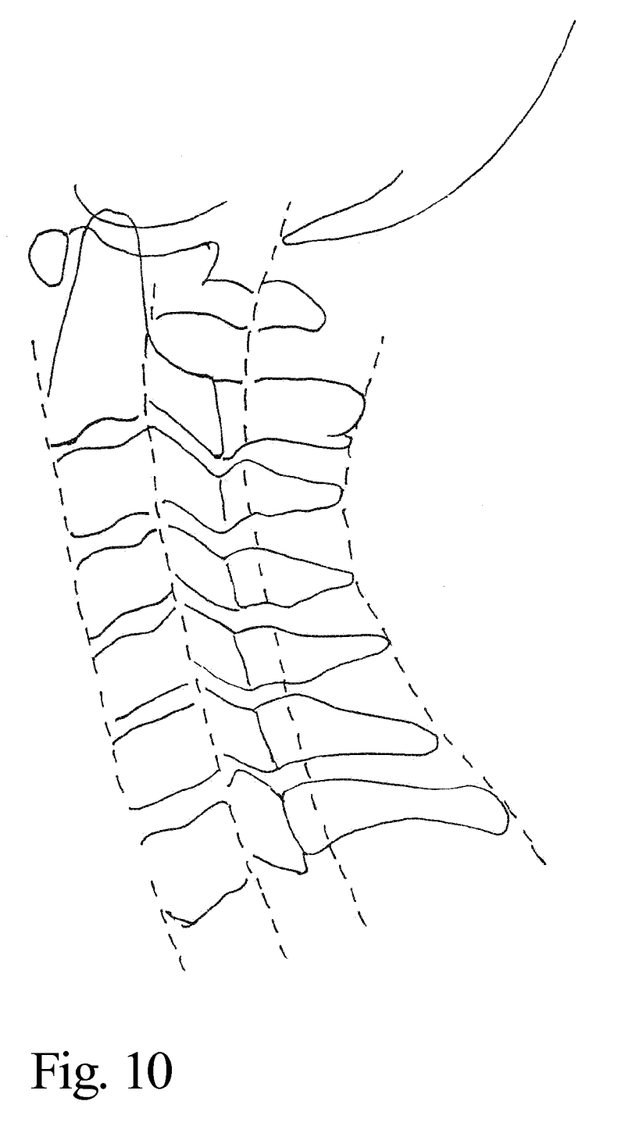
FIG. 10 illustrates that the sagittal roll increases from cephalad to caudad.
Figure 11:
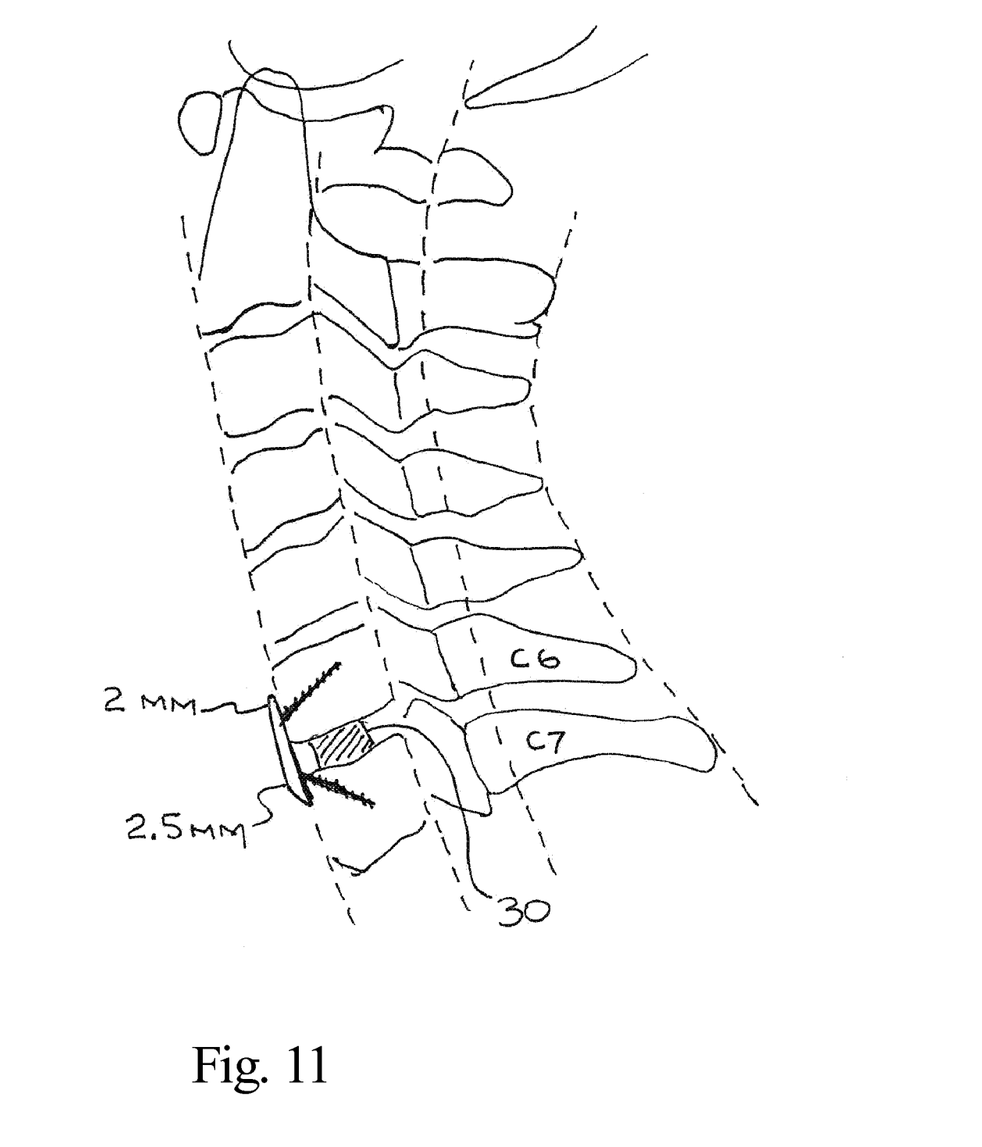
FIG. 11 illustrates a one level fusion.
Figure 12:
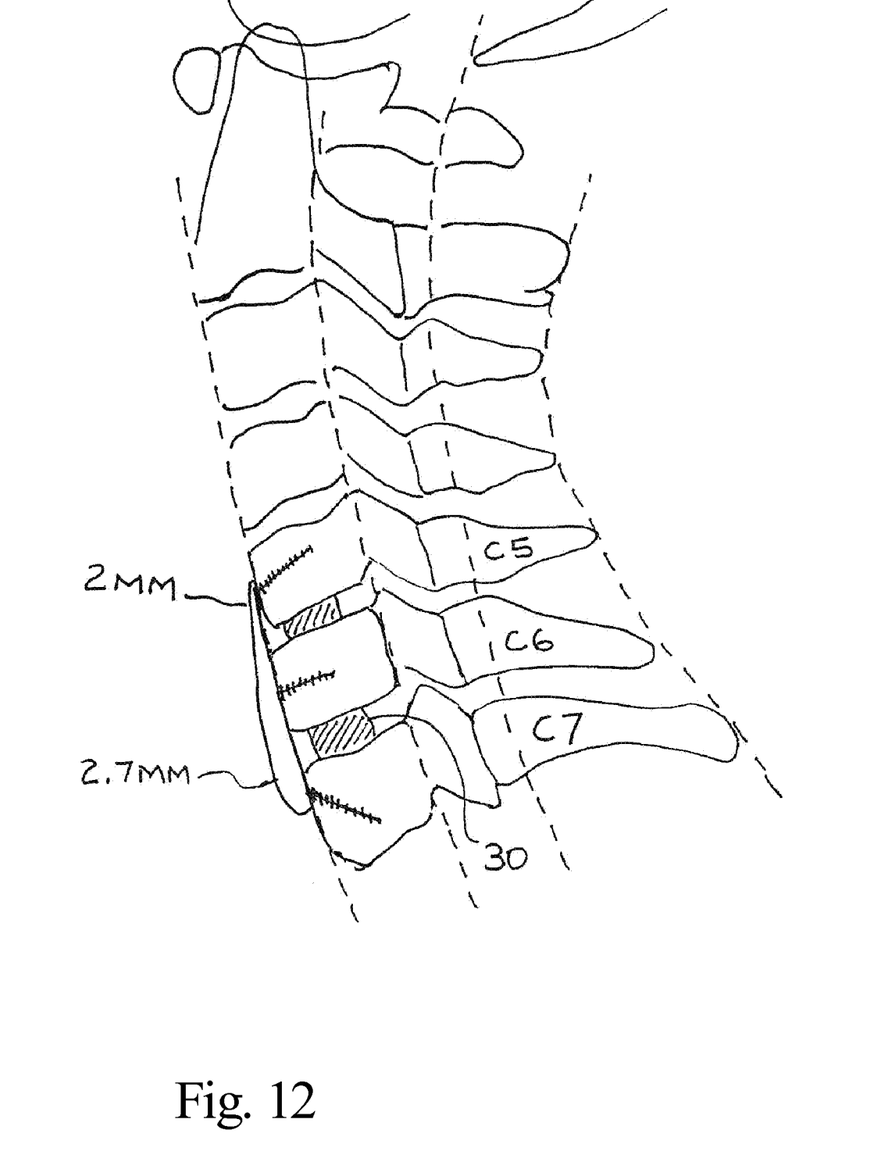
FIG. 12 illustrates a two level fusion.
Figure 13:
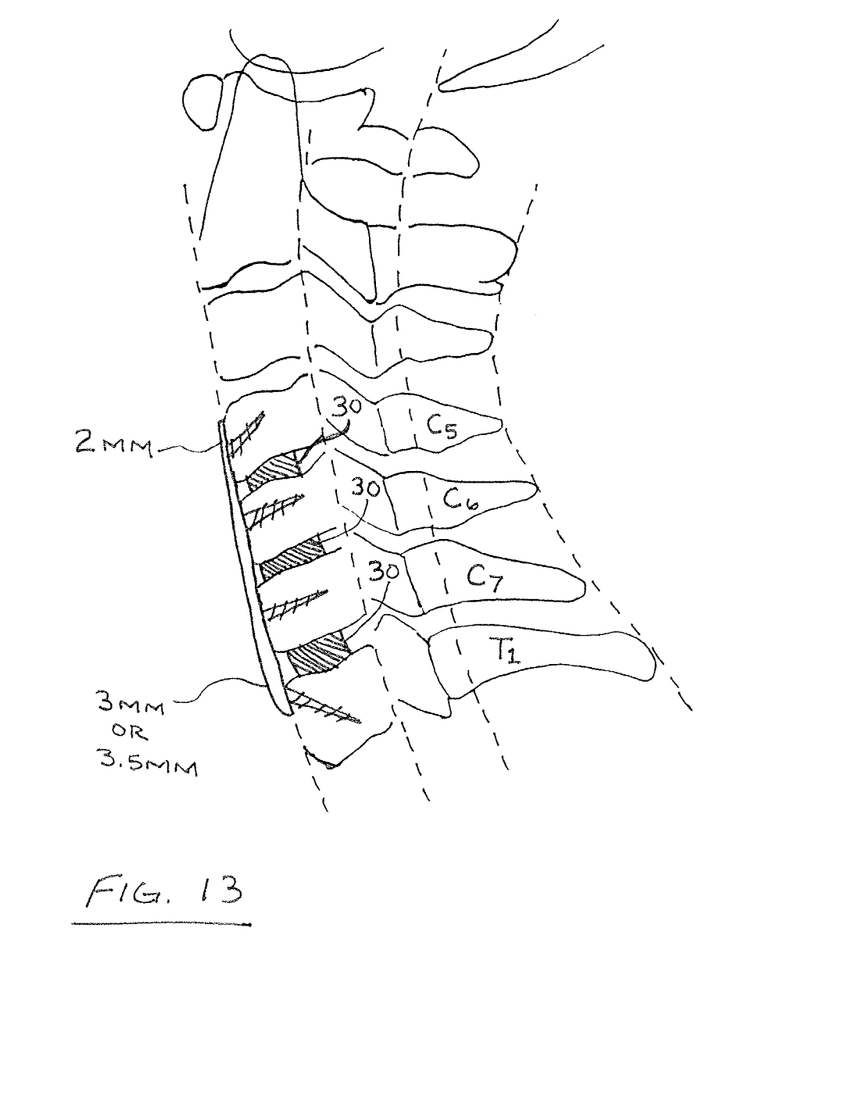
FIG. 13 illustrates a three level fusion.

The disclosed plate with graduated thickness will require standard discectomy and inter-body bone graft placement. Additionally, as shown in FIG. 9, it is contemplated that the plate will be first positioned through the use of wire guides cephalad and caudad to ensure that the orientation and position are optimal prior to drilling and installation of the screws. It is contemplated that the plates would be provided in various lengths, allowing the surgeon to first measure length (in line) between the locations where the screws are to be placed, and then select the proper size plate and positioning the plate by sliding the plate along the wire guides 34.

Surgical Method: Guide Wire Advantages

The use of the wire guides will result in accurate plate length selection and subsequent plate placement (cephalad/caudad and medial/lateral). This avoids plate misalignment, which can cause portions of the plate to encroach on adjacent disc spaces. Furthermore, the use of wire guided 34 holds plate in position for middle vertebral body drilling and screw placement. In a two or three level fusion, the screws between the first end and the second end would be substantially normal to the plate. These central screws 36 would be installed first. Once these initial screws have been inserted then the surgeon would then remove guide wires 34 and then drill and place cephalad and caudad compression-lag screws leading to graft compression. In other words, the screws at the first end and at the second end would be installed after the screws between the first end and the second end have been installed.

Design Details of Highly Preferred Embodiment

According to a highly preferred example of the plate, the proximal plate thickness (first end 14) should be about 2.3 mm (first thickness $T_1$). The distal plate thickness (second thickness $T_2$ at the second end 18) would be as follows (corresponding to fusion levels):
  1—level 2.5 nm
  2—level 2.7 mm
  3—level 2.9 m
  4—level about 3.1 nm Design Details It is contemplated that the following dimensions, geometries would used in preferred examples of the invention:
Plate maximum width: 17 mm
Plate at narrowest: 13 mm
Screw convergence angle 36: 5 degrees Screw Design It is contemplated that the following dimensions, geometry will be used with a highly preferred example:
  length
    Proximal (first end): 14 mm overall length, 12 mm working length;
    Distal (second end): 17 mm overall length, 14 mm working length.
  Diameter
    Primary screws: 4.25 mm consistent outer diameter bone threads
    Rescue screws: 4.45 mm consistent outer diameter bone threads
    Primary and Rescue screws: increasing core diameter Screw/Plate Locking Mechanism
    Interference fit screw heads will be used to lock the screws in place. The plate has female square buttress threads 40. Screw at plate interface 42 has male square buttress threads. Outer diameter of screw male buttress threads 4.5 mm (Primary and Rescue). The bone threads and male buttress threads have same pitch, but the screw has increasing inner core diameter of male buttress thread. This will result in an interference fit with the increasing core diameter and square buttress threads resulting in cold welding as the threads of the screw are turned into the threads in the plate. It is preferred that the interference and resulting cold welding will be such that the initial screw placement will require a first torque wrench setting (providing about 2-3 ft-lbs) and then final torque wrench setting providing final locking, or second torque wrench (providing approximately 15-20 ft-lbs).

In sum, the disclosed invention and method will provide increased rigidity where it is needed most, and that is to provide active graft compression. Additionally, the method provides accurate and reliable plate placement, which ameliorate issues of plate encroachment into healthy spaces.

Thus it can be appreciated that the above-described embodiments are illustrative of just a few of the numerous variations of arrangements of the disclosed elements used to carry out the disclosed invention. Moreover, while the invention has been particularly shown, described and illustrated in detail with reference to preferred embodiments and modifications thereof, it should be understood that the foregoing and other modifications are exemplary only, and that equivalent changes in form and detail may be made without departing from the true spirit and scope of the invention as claimed, except as precluded by the prior art.

What is claimed is:

1. A cervical plate system for creating a fusion between a first cervical vertebra and a second cervical vertebra the first cervical vertebra being in a cephaldad relation to the second cervical vertebra, the system comprising:
a cervical plate comprising:
a curved plate body having a concave side that extends between a first end of a first thickness and a second end of a second thickness, the first end being adapted for attachment to the first vertebra in a cephalad relation to the plate body, the first end having an aperture adapted for accepting a screw of a first screw length, the screw of a first screw length having a first screw threaded portion and a first screw head that cooperates with the aperture of the first end such that the first screw extends from concave portion of the curved plate body when the first screw head is in contact with the aperture in the first end of the curved plate, the second end of the plate being adapted for attachment to the second vertebra a caudad relation to the plate body, the second end of the plate further having an aperture adapted for accepting a screw of a second screw length having a second screw head and a second screw threaded portion, the aperture of the second end retaining the screw of a second screw length at an angle to the screw of a first screw length, so that the threaded portion the screw of a first screw length and the threaded portion the screw of a second screw length diverge from one another, with the first screw head and the second screw head being closer to one another than the first screw threaded portion and the second screw threaded portion;
the first thickness of the curved plate body being smaller than the second thickness of curved plate body, and the plate body transitioning from the first thickness to the second thickness in a graduated manner; and
at least one graft that adapted for positioning between the concave side of the curved plate and between the first cervical vertebra and the second cervical vertebra, so that that divergence of the screw of a first screw length from the screw of a second screw length plate causes compression of the graft between the first and second vertebra when the screw of a first screw length is fastened through the aperture on the first end of the cervical plate and the screw of a second screw length is fastened through the aperture on the second end of the cervical plate.

2. A cervical plate system for creating a multiple level fusion between a first cervical vertebra, a second cervical vertebra, and a third cervical vertebra, the first cervical vertebra being in a cephalad relation to the second cervical vertebra, and the second cervical vertebra being in a cephalad relation to the third cervical vertebra, the system comprising:
a cervical plate comprising:
a curved plate body having a concave lower side that extends between a first end of a first thickness and a second end of a second thickness, the first end being adapted for attachment to the first vertebra in a cephalad relation to the plate body, the first end having an aperture adapted for accepting a screw of a first screw length, the screw of a first screw length having a first screw threaded portion and a first screw head that cooperates with the aperture of the first end such that the first screw extends from the concave lower side of the curved plate body when the first screw head is in contact with the aperture in the first end of the curved plate;
the second end of the plate being adapted for attachment to the third vertebra a caudad relation to the plate body, the second end of the plate further having an aperture adapted for accepting a screw of a second screw length having a second screw head and a second screw threaded portion, the aperture of the second end retaining the screw of a second screw length at an angle to the screw of a first screw length, so that the threaded portion the screw of a first screw length and the threaded portion the screw of a second screw length diverge from one another, with the first screw head and the second screw head being closer to one another than the first screw threaded portion and the second screw threaded portion;
the plate body being of a first thickness at the first end and of a second thickness at the second end, the first thickness being smaller than the second thickness, and the plate body transitioning from the first thickness to the second thickness in a graduated manner;
at least one aperture adapted for accepting at least one central screw, the at least one aperture adapted for accepting central screw being positioned substantially normal to the concave lower surface between the aperture adapted for accepting a screw of a first screw length and the aperture adapted for accepting a screw of a second screw length; and
at least at least two grafts, at least one of the two grafts being adapted for positioning between the concave side of the curved plate and between the first cervical vertebra and the second cervical vertebra, and at least one of the two grafts being adapted for positioning between the concave side of the curved plate and between the second cervical vertebra and the third cervical vertebra, so that that divergence of the screw of a first screw length from the screw of a second screw length plate causes compression of the at least two grafts between the first and second vertebra, and the second and third vertebra when the screw of a first screw length is fastened through the aperture on the first end of the cervical plate and the screw of a second screw length is fastened through the aperture on the second end of the cervical plate.

3. A cervical plate system according to claim 2 wherein the curved plate body further comprises a pair of guide wires, the guide wires cooperating with the aperture in the first end and the aperture in the second end respectively for locating the plate before drilling and inserting screws in the aperture adapted for accepting central screw.

4. A cervical plate system according to claim 2 wherein the screw of a first screw length from the screw of a second screw length are of the same overall length.

* * * * *